(12) United States Patent
Kimsey

(10) Patent No.: US 6,373,395 B1
(45) Date of Patent: Apr. 16, 2002

(54) MOISTURE DETECTOR

(76) Inventor: Paul Kimsey, Aswardby Water Mill, Sausthorpe, Spilsby, Lincolnshire, PE23 4LB (GB)

( * ) Notice: Subject to any disclaimer, the term of this patent is extended or adjusted under 35 U.S.C. 154(b) by 0 days.

(21) Appl. No.: 09/700,961

(22) PCT Filed: May 28, 1999

(86) PCT No.: PCT/GB99/01710

§ 371 Date: Nov. 21, 2000

§ 102(e) Date: Nov. 21, 2000

(87) PCT Pub. No.: WO99/63497

PCT Pub. Date: Dec. 9, 1999

(30) Foreign Application Priority Data

Jun. 3, 1998 (GB) ............................................. 9811779
Aug. 21, 1998 (GB) ............................................. 9818164

(51) Int. Cl.$^7$ ............................................. G08B 21/00
(52) U.S. Cl. ................ 340/602; 340/604; 340/573.5; 604/361
(58) Field of Search ................ 340/602, 604, 340/573.1, 603, 573.5, 605; 128/885, 886, 734, 638; 604/361, 364, 358; 200/61.04, 61.05

(56) References Cited

U.S. PATENT DOCUMENTS

| | | | | |
|---|---|---|---|---|
| 4,106,001 A | * | 8/1978 | Mahoney ................ | 340/604 |
| 5,036,859 A | * | 8/1991 | Brown ................ | 128/734 |
| 5,266,928 A | * | 11/1993 | Johnson ................ | 340/604 |
| 5,392,032 A | * | 2/1995 | Kline et al. ................ | 340/604 |
| 5,469,145 A | * | 11/1995 | Johnson ................ | 340/604 |
| 5,557,263 A | * | 9/1996 | Fisher et al. ................ | 340/605 |
| 5,570,082 A | * | 10/1996 | Mahgerefteh et al. ....... | 340/604 |
| 5,760,694 A | * | 6/1998 | Nissim et al. ................ | 340/604 |
| 5,796,345 A | * | 8/1998 | Leventis et al. ............ | 340/604 |
| 5,838,240 A | * | 11/1998 | Johnson ................ | 340/604 |
| 5,903,222 A | * | 5/1999 | Kawarizadeh et al. ...... | 340/604 |
| 6,097,297 A | * | 8/2000 | Fard ................ | 340/604 |
| 6,200,250 B1 | * | 3/2001 | Janszen ................ | 493/383 |

FOREIGN PATENT DOCUMENTS

GB 2250121 5/1992

OTHER PUBLICATIONS

Patent Abstracts of Japan vol. 8, No. 248.

* cited by examiner

*Primary Examiner*—Daniel J. Wu
*Assistant Examiner*—Toan Pham
(74) *Attorney, Agent, or Firm*—Ira S. Dorman

(57) ABSTRACT

A detector unit (1) which, in the presence of moisture, operates a remote alarm via a wire-less link is contained within a sealed liquid-impermeable housing (2). The unit is powered by electrical charge stored in a capacitor, which may be rapidly recharged by inductive coupling. Remote sensing electrodes (69, 70) are formed by depositing an electrically conductive ink onto a disposable moisture-absorbent tail (65).

8 Claims, 4 Drawing Sheets

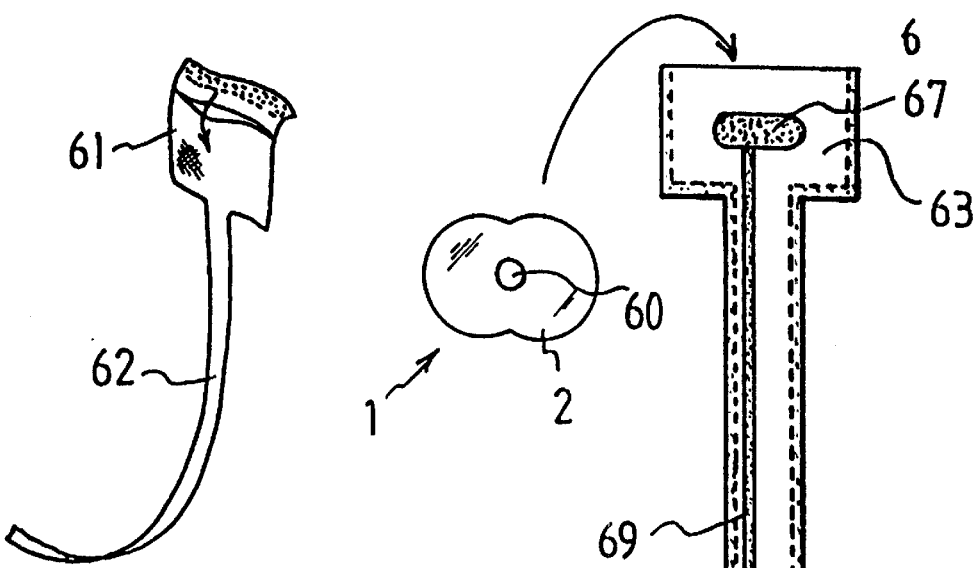
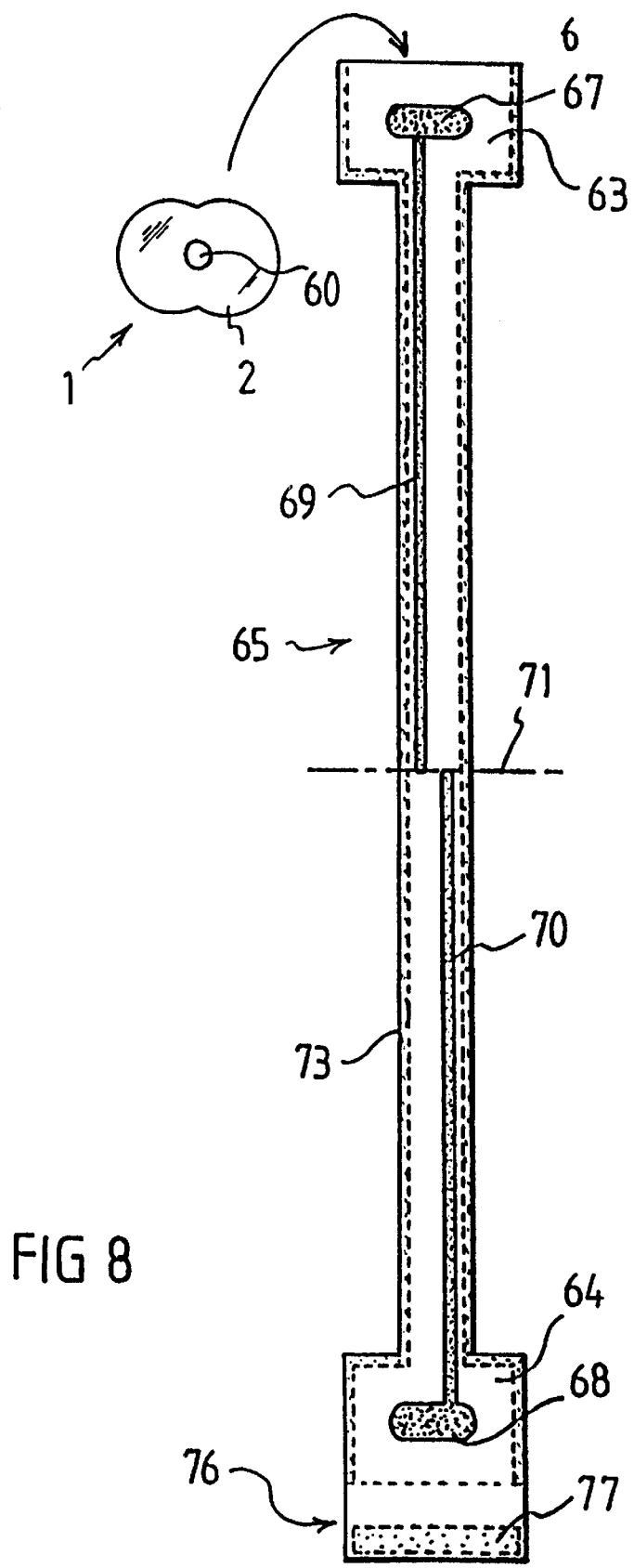
FIG 7
FIG 8

MOISTURE DETECTOR

TECHNICAL FIELD OF THE INVENTION

This invention relates to a moisture detector, particularly, but not exclusively, for detecting urine.

BACKGROUND

It is already known, e.g. from GB 2 219 679 A, to use a battery-operated moisture detector in a babies nappy (diaper). When the nappy becomes wet a radio signal is sent to a remote indicator which generates an audible signal to indicate that the nappy requires changing.

The present invention seeks to provide a new and inventive form of moisture detector.

SUMMARY OF THE INVENTION

The present invention proposes a moisture detector comprising a detector unit which is arranged to operate a remote alarm via a wire-less link when moisture is present, in which the detector unit is powered by electrical charge stored in capacitor means.

The capacitor means may comprise a single capacitor or a bank of capacitors.

In a preferred form the detector unit comprises a sealed liquid-impermeable housing containing said capacitor means, and an external moisture sensor.

The moisture sensor preferably comprises a pair of moisture-sensing electrodes. In a preferred form of the device the moisture-sensing electrodes are remote from the housing of the detector unit. The electrodes are preferably incorporated in a moisture-absorbent tail and are preferably formed by depositing an electrically-conductive ink onto a flexible moisture-absorbent strip.

BRIEF DESCRIPTION OF THE DRAWINGS

The following description and the accompanying drawings referred to therein are included by way of non-limiting example in order to illustrate how the invention may be put into practice. In the drawings:

FIG. 7 is a general view of further modified form of the detector unit; and

FIG. 8 is a more detailed view of the detector unit of FIG. 7.

DETAILED DESCRIPTION OF THE DRAWINGS

The equipment comprises three separate units, namely a detector unit (FIG. 1) to be placed in a babies nappy, a receiver unit (FIG. 3) carried by an adult (normally the babies mother), and a charger unit (FIG. 5) for re-charging the detector unit as necessary.

Figure 1:
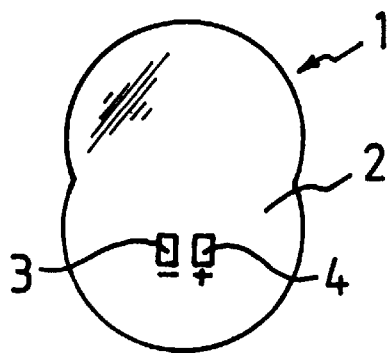
FIG. 1 is a general view of a detector unit of a moisture detector in accordance with the invention.

Referring to FIG. 1, the detector unit 1 has a soft encapsulating sealed moisture-proof outer case 2 of a soft and flexible material such as latex rubber, silicone rubber or plastic, which encloses the electronic circuitry to prevent contact With urine. The electronics are further encapsulated in resin within the case 2 to provide mechanical protection. Two electrodes 3 and 4 of corrosion-resistant metal are exposed on the external surface of the case 2, which serve a dual function of moisture sensors and providing contacts via which the detector unit can be re-charged. When placed in the nappy the sensor electrodes are placed in contact the moisture-absorbent material of the nappy, but preferably not in contact with the babies skin to prevent normal skin moisture from triggering the unit. In any event it is preferable to set the detection threshold such that the unit is not triggered by normal skin contact.

Figure 2:
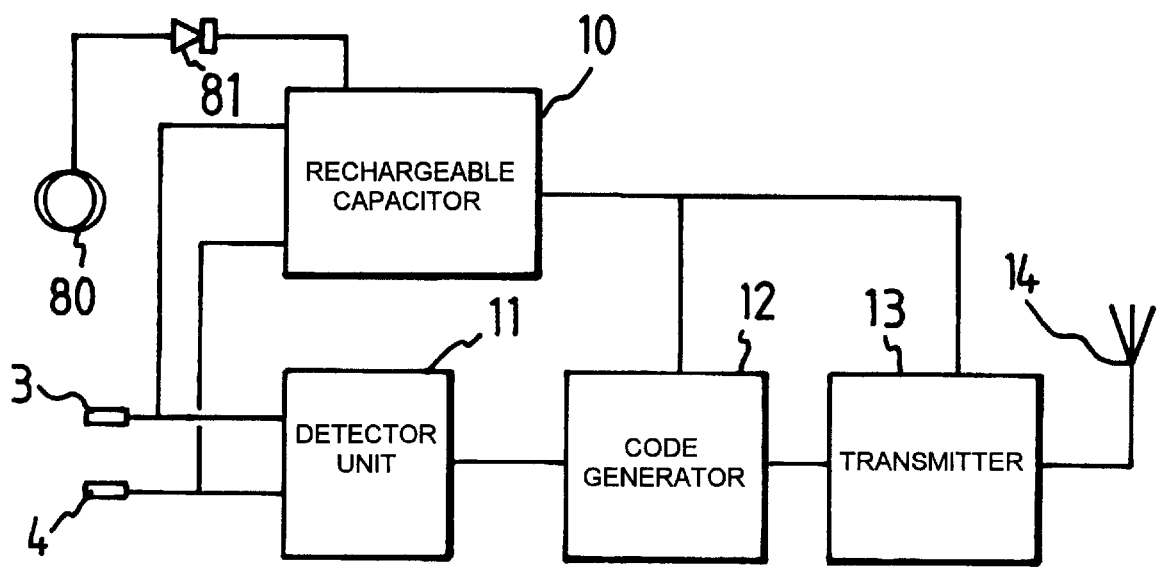
FIG. 2 is a block circuit diagram of the detector unit.

Referring to FIG. 2, the electronics is powered from a rechargeable capacitor 10 comprising thin conductive layers separated by a thin layer of an electrical insulating material. A tantalum or electrolytic capacitor may be used, e.g. of wet type double layer electrolytic construction, having a value from serval thousand microfarads up to several farads. A detector circuit 11 monitors the electrical impedance between the electrodes 3 and 4 and signals a microprocessor-based code generator 12 when the impedance falls below a predetermined threshold due to presence of moisture. Upon receiving the signal from the detector 11 the generator 12 activates a high frequency radio transmitter 13 which transmits the code by frequency modulation via an aerial 14, also enclosed within the case 2.

The detector 11, generator 12 and transmitter 14 employ CMOS technology so that the circuit is of a high supply impedance and therefore draws a very low current from the capacitor 10. By using high impedance electronics the current consumption can be reduced sufficiently to allow the device to operate for more than an hour without recharging. The transmitter 14 only generates a few microwatts of radio frequency power, but this is sufficient to be detected over a distance of about 50 metres. The use of a capacitor has several advantages. Firstly, it eliminates corrosive and/or toxic substances which are widely used in batteries. Secondly, a capacitor does not suffer from memory problems associated with the use of rechargeable batteries which reduces their storage capacity, so that the service life of the unit is considerably increased. Thirdly, a capacitor can be fully charged in a matter of seconds, much less than the time normally taken to change a nappy. The unit can therefore be used without interruption and no battery changing is necessary.

The capacitor power source 10 is provided with a charge monitor circuit which signals the microprocessor 12 when the capacitor voltage falls below a predetermined level. The microprocessor then generates a different code which is transmitted by the unit 13 to signal that the detector unit requires recharging.

Figure 3:
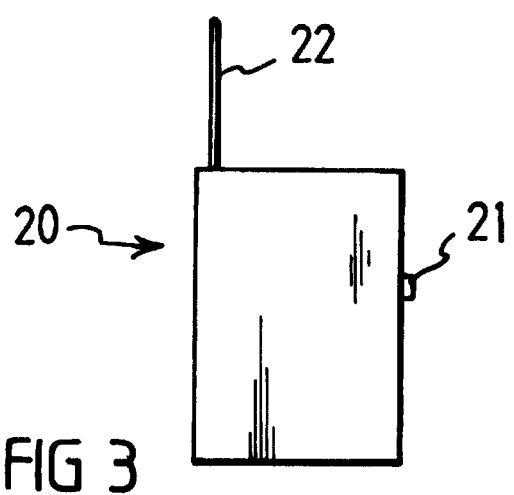
FIG. 3 is a general view of a receiver unit of the moisture detector.
Figure 4:
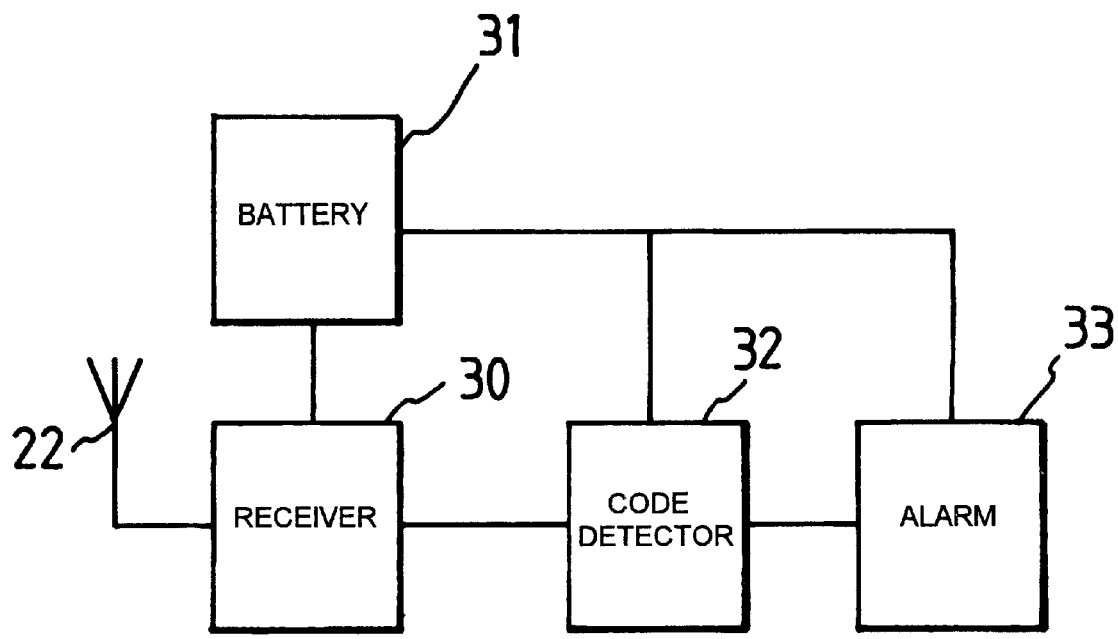
FIG. 4 is a block circuit diagram of the receiver unit.

Referring to FIG. 3, the portable receiver unit 20 incorporates an on/off switch 21 and a receiving aerial 22, which although shown externally will normally be internal to the case 23. The unit may be provided with a mounting clip (not shown) and houses a radio receiver 30 as shown in FIG. 4. The receiver unit electronics are powered from a conventional battery supply 31 so that there is no need for frequent recharging. Upon receiving a signal from the detector unit 1 a microprocessor-based code detector 32 interprets the code and operates an alarm device 33 to signal either that the nappy is wet or that the detector charge is low. Different coloured LEDs could be used to indicate the two different alarm conditions. Both states are signalled to the mother by a beeper that continues to sound until the receiver unit is switched off.

Figure 5:
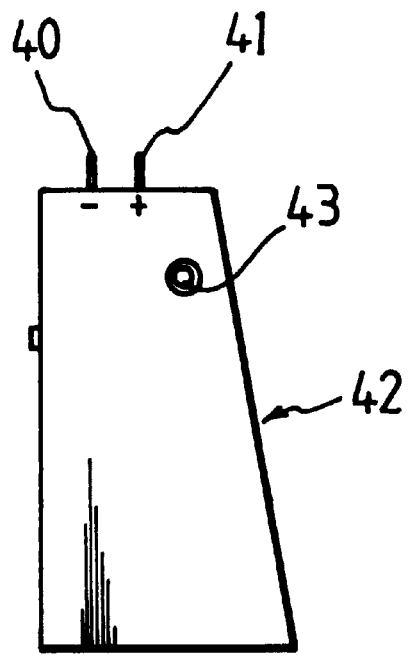
FIG. 5 is a general view of a charger unit for use with the detector unit.

When removed from the nappy the detector unit 1 may be recharged by placing the electrodes 3 and 4 against two contacts 40 and 41 of a mains-powered charging unit 42, shown in FIG. 5. The detector may be held in a cradle, rather like a mobile phone charger. When the detector unit draws current to recharge the capacitor 10 an LED 43 on the charger unit illuminates to confirm that a good electrical contact exists. The capacitor may be arranged to receive power via a rectifier so that should the detector unit be connected the wrong way round no harm will result, but the capacitor will not charge and the LED will not illuminate. After about 30 seconds, when the capacitor reaches full charge (about 5 volts), the LED fades to indicate that the detector is ready for use.

A preferred arrangement is to charge the capacitor by inductive coupling with the charger whereby an alternating current is induced in an electromagnetic coil 80 within the housing 2 (FIG. 2) and is rectified by diode 81 to charge the capacitor 10. This eliminates the need for a physical connection with the charger. Again, charging is very rapid.

The detector unit 1 should be wiped clean with a damp cloth or tissue before being re-used.

Figure 6:
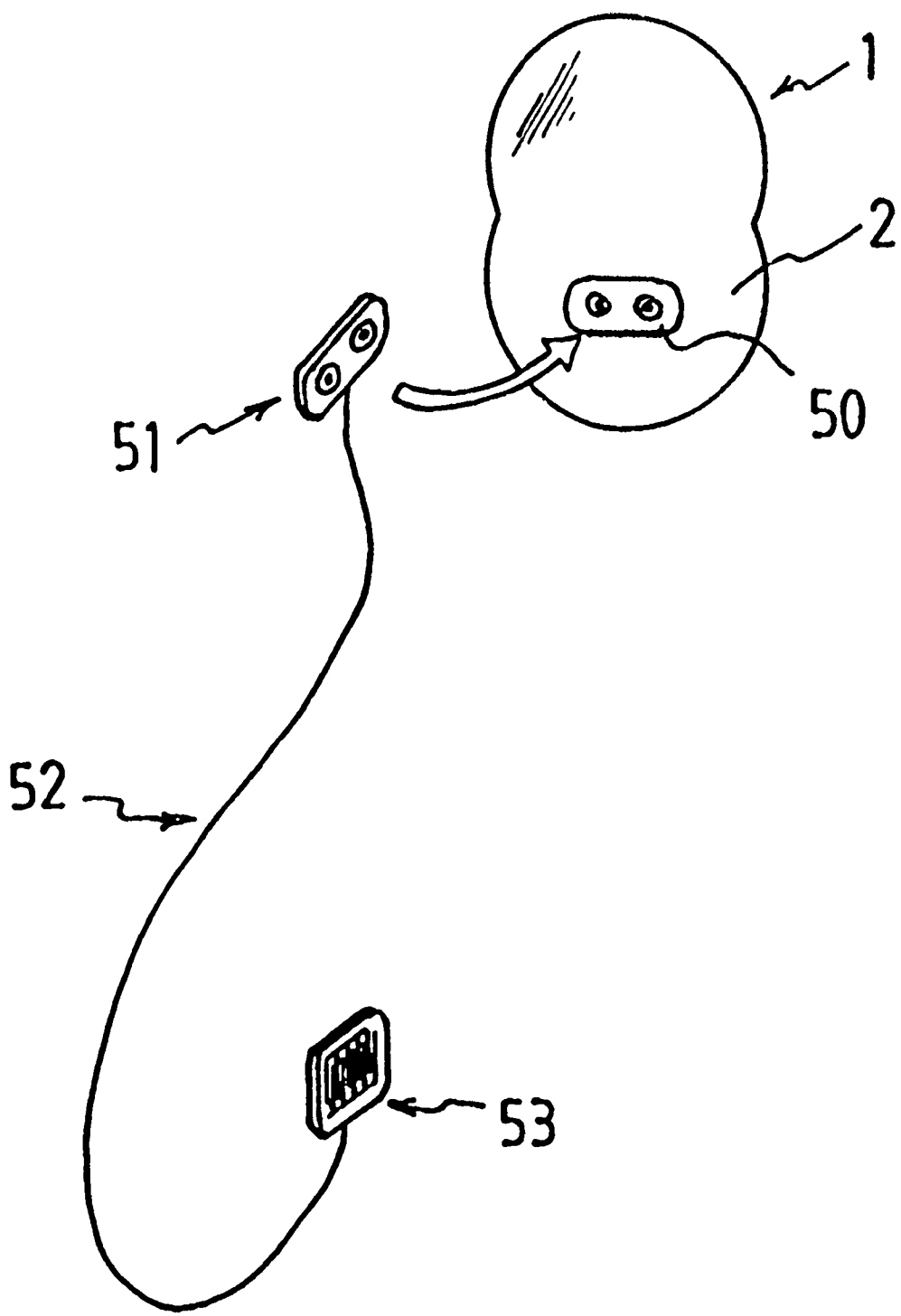
FIG. 6 is a general view of a modified form of the detector unit.

The modified detector unit 1 shown in FIG. 6 again has a soft encapsulating sealed moisture-proof outer case 2 which encloses the electronic circuitry. However, the electrodes 3 and 4 are replaced by a two-pin connector 50 to which a mating connector 51 can be attached. The connector 51 is joined by a twin insulated wire 52 to a remote moisture sensor 53 which, by way of example, could comprise a pair of closely disposed tracks carried on the surface of an insulating plate. This form of the detector unit 1 can be mounted outside the nappy within the babies clothing or tucked inside the waist band of the nappy. The sensor 53 is inserted into the nappy in contact with the moisture-absorbing material so that when the nappy becomes wet with urine a signal is sent to the electronics to trigger an alarm as described above. However the remote sensor has the advantage that the unit 1 is not in direct contact with urine and therefore requires less frequent cleaning. The sensor 53 is simply uncoupled at the connectors 50/51 and sterilised or discarded.

The capacitor power source within the unit 1 can be recharged via the connector 50 or preferably by inductive coupling as described above.

For cosmetic reasons it is desirable to incorporate the wires 52 into a flexible tape, sleeve or nappy liner which is discarded along with the connector 51 and sensor 53. Furthermore, the sensor 53, wires 52 and connector 51 could be integrally incorporated into a disposable nappy so that they are discarded along with the nappy, the unit 1 still being a reusable item. The detector unit which is shown in FIGS. 7 and 8 allows this to be achieved in an inexpensive but very effective manner. The unit 1 again includes a soft moisture-proof case 2 which encloses the electronic circuitry. In place of the two-pin connector 50 there are two electrical contacts 60 mounted on opposite sides of the case 2. The unit 1 is inserted into a disposable pocket 61 which has an integral sensing tail 62.

The pocket 61 and tail 62 are formed from a strip 65 of strong moisture-absorbent tissue paper like material having enlarged areas 63 and 64 at opposite ends to form the pocket 61. On one side only of the sheet an electrically-conductive layer is deposited by a printing process using an electrically-conductive carbon-containing ink. A contact area 67, 68 is deposited in the centre of each area 63 and 64 with respective conductive tracks 69 and 70 which end mid-way along the strip. The tracks 69 and 70 are not mutually joined and are offset towards opposite edges of the strip so that when the strip is folded along a centre line 71 the two tracks still do not make electrical contact along the tail 62. The two superimposed halves of the strip 65 are secured together by an adhesive 73 which extends along the strip and around the periphery of each end area 63, 64. However, the top of the pocket 61 remains open so that the detector unit 1 can be inserted, whereupon the contacts 60 make electrical contact with the conductive areas 67 and 68. In order to retain the detector unit in the pocket 61 a flap 76 can be formed by an extended part of the enlarged area 64, which may be folded over and secured to the outer surface of the area 63 by means of a pressure-sensitive adhesive 77. The adhesive 77 can conveniently be protected by a peelable backing sheet (not shown) prior to use.

The pocket 61 containing the detector unit can be mounted outside the nappy within the babies clothing or tucked inside the waist band of the nappy. The sensing tail 62 is inserted into the nappy so that when the tissue-paper-like material becomes wet with urine the electrical resistance between the tracks 68 and 69 is reduced and a signal is sent to the electronics to trigger an alarm, as already described. After the alarm has been triggered the case 2 is removed from the pocket 61 which is discarded with the attached sensing tail 62. The case 2 can be recharged and sterilised if necessary and replaced into a fresh pocket 61 for re-use.

Although the above description refers specifically to use in a babies nappy the moisture detector has a wider application. For example, the detector could be used by incontinent adults or bed wetters. Similarly, the detector unit can be used to sense other kinds of moisture other than urine.

It will be appreciated that the features disclosed herein may be present in any feasible combination. Whilst the above description lays emphasis on those areas which, in combination, are believed to be new, protection is claimed for any inventive combination of the features disclosed herein.

What is claimed is:

1. A moisture detector which includes:
    a detector unit (1) having a liquid-impermeable housing (2); moisture-sensing means (3, 4; 53; 65) which has a pair of moisture-sensing electrodes (3, 4; 69, 70); a remote alarm (20) which is operable by the detector unit via a wire-less link when moisture is present at the moisture-sensing electrodes; and a charging unit (42) for receiving the detector unit to supply electrical charge to the capacitor means, said detector unit (1) including capacitor means (10) for storing electrical charge to power the detector unit, and said charging unit being separate from said detector unit and said moisture-sensing means.

2. A moisture detector according to claim 1, in which the moisture-sensing electrodes comprise an electrically-conductive ink (69, 70) deposited on a flexible moisture-absorbent strip (65).

3. A moisture detector according to claim 2, in which the moisture-absorbent strip comprises two opposed moisture-absorbent layers with ink deposited on mutually-opposed faces of the two layers.

4. A moisture detector according to claim 3, in which the two layers form a pocket (61) for receiving the detector unit.

5. A moisture detector according to claim 4, in which the detector unit is electrically connected with the moisture-sensing electrodes via areas of electrically conductive ink (67, 68) deposited on the inside of the pocket.

6. A moisture detector according to claim 1, in which the detector unit and the charging unit include inductive coupling means (80) for supplying electrical charge to the capacitor means.

7. A moisture detector which includes:

a detector unit (1) having a liquid-impermeable housing (2); moisture-sensing means (3, 4; 53; 65) for attachment to the detector unit and which has a pair of moisture-sensing electrodes (3, 4; 69, 70) for location remote from the detector unit; and a remote alarm (20) which is operable by the detector unit via a wire-less link when moisture is present at the moisture-sensing electrodes; characterised in that the detector unit (1) includes capacitor means (10) for storing electrical charge to power the detector unit when attached to the moisture-sensing means, and a charging unit (42) is provided for receiving the detector unit to supply electrical charge to the capacitor means (10), said moisture-sensing electrodes comprising an electrically-conductive ink (69, 70) deposited on a flexible moisture-absorbent strip (65) comprised of two opposed moisture-absorbent layers with ink deposited on mutually-opposed faces of the two layers, said layers forming a pocket for receiving the detector unit, and said detector unit being electrically connected to the moisture-sensing electrodes via areas of electrically conductive ink (67, 68) deposited on the inside of the said pocket.

8. A moisture detector according to claim 7, in which the moisture-absorbent strip comprises a single length of moisture-absorbent material which is folded double to form the two layers.

* * * * *